(12) United States Patent
Ramsey et al.

(10) Patent No.: US 6,524,456 B1
(45) Date of Patent: Feb. 25, 2003

(54) MICROFLUIDIC DEVICES FOR THE CONTROLLED MANIPULATION OF SMALL VOLUMES

(75) Inventors: J. Michael Ramsey, Knoxville, TN (US); Stephen C. Jacobson, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/408,060

(22) Filed: Sep. 29, 1999

Related U.S. Application Data (60) Provisional application No. 60/148,502, filed on Aug. 12, 1999.

(51) Int. Cl.[7] ..................... G01N 27/447; G01N 27/453
(52) U.S. Cl. ................. 204/450; 204/600; 422/82; 422/100; 436/53
(58) Field of Search ............................... 204/450, 451, 204/600, 601, 453, 604; 422/99, 100, 82; 436/53

(56) References Cited

U.S. PATENT DOCUMENTS 5,750,015 A * 5/1998 Soane et al. ............... 204/454
6,130,098 A * 10/2000 Handique et al. .......... 422/100
6,150,119 A * 11/2000 Kopf-Sill et al. .......... 435/7.1

* cited by examiner

Primary Examiner—Jill Warden
Assistant Examiner—Alex Noguerola
(74) Attorney, Agent, or Firm—Dann, Dorfman, Herrell and Skillman, P.C.

(57) ABSTRACT

A method for conducting a broad range of biochemical analyses or manipulations on a series of nano- to subnanoliter reaction volumes and an apparatus for carrying out the same are disclosed. The method and apparatus are implemented on a fluidic microchip to provide high serial throughput. The method and device of the invention also lend themselves to multiple parallel analyses and manipulation to provide greater throughput for the generation of biochemical information. In particular, the disclosed device is a microfabricated channel device that can manipulate nanoliter or subnanoliter biochemical reaction volumes in a controlled manner to produce results at rates of 1 to 10 Hz per channel. The individual reaction volumes are manipulated in serial fashion analogous to a digital shift register. The method and apparatus according to this invention have application to such problems as screening molecular or cellular targets using single beads from split-synthesis combinatorial libraries, screening single cells for RNA or protein expression, genetic diagnostic screening at the single cell level, or performing single cell signal transduction studies.

55 Claims, 5 Drawing Sheets

MICROFLUIDIC DEVICES FOR THE CONTROLLED MANIPULATION OF SMALL VOLUMES

Applicants claim the benefit of priority of U S. Provisional Application No. 60/148,502, filed on Aug. 12, 1999.

The U.S. Government has a paid-up license in this invention and the right in limited circumstances to require the patent owner to license others on reasonable terms as provided for by the terms of Contract No. DE-AC05-96OR22464 awarded by the U.S. Department of Energy.

The United States Government has rights in this invention pursuant to contract no. DE-AC05-00OR22725 between the United States Department of Energy and UT-Battelle, LLC.

FIELD OF THE INVENTION

This invention relates to a microfabricated fluidic device, and in particular, to such a device that is configured for forming and transporting a series of minute volume segments of a material and for storage, retrieval, and analysis thereof and to a method for forming, transporting, storing, and retrieving such a series of minute volume segments.

BACKGROUND OF THE INVENTION

A number of elementary microfabricated fluidic devices have been demonstrated over the past few years. Although many of these fluidic devices are quite simple, they are demonstratively powerful in addressing many realistic applications and may well revolutionize the way that biochemical separations are performed. The majority of the demonstrations have involved transferring known chemical measurement techniques, such as electrophoresis or liquid chromatography, onto microfabricated platforms. Such demonstrations suggest that microfabricated separation devices will be quite useful for improving the time and cost associated with collecting information from such experiments. However, the known devices have not exploited the new experimental approaches that such microfabricated devices potentially enable. We believe that through improvements in microfluidic control, new more powerful biochemical experimental paradigms will arise.

The area of microfabricated fluidics that has received the most attention is electrokinetically driven processes. Electrokinetic fluid manipulations have been demonstrated for mixing and reacting reagents, injection or dispensing of samples, and chemical separations. Electrically driven separation techniques such as capillary electrophoresis (CE), open channel electrochromatography (OCEC) and micellar electrokinetic capillary chromatography (MEKC) have been demonstrated by a number of research groups. Both dsDNA fragments and sequencing products have been sized using microchip capillary gel electrophoresis coupled with laser induced fluorescence detection. Less conventional electrophoretic separations have been studied in post arrays using DC and pulsed electric fields. In addition fluorescence-based competitive immunoassays have been demonstrated using microchip electrophoretic separation of bound and free labeled antigen. These miniature devices have shown performance either equivalent to or better than conventional laboratory devices in all cases investigated and appear to offer the rare combination of "better-faster-cheaper" simultaneously. Microchip separation devices exhibit speed advantages of one to a few orders of magnitude over conventional approaches. The efficiency of electrophoretic separations under diffusion limited conditions is proportional to the voltage drop experienced by the sample. These diffusion limiting conditions can be achieved for short separation distances on microchips due to the narrow axial extent of the injection plugs that are generated. The time of analysis decreases quadratically with separation distance at constant applied potential, which gives a fundamental advantage to microchip-based electrophoretic separations.

Other significant advantages of microchip based chemical separations are the small volumes that can be analyzed, the ability to monolithically integrate sample processing and analysis, and the low cost of replication which makes possible highly parallel analyses. All of these factors are consistent with high throughput analysis and reductions in cost and time to generate biochemical information. Early efforts demonstrating integration of sample processing include post-separation and pre-separation derivatization of amino acids coupled to electrophoretic separations. On-chip DNA restriction digestions and PCR amplifications have been coupled with electrophoretic fragment sizing on integrated monolithic microchips. Cell lysis, multiplex PCR, and CE analysis were performed on plasmic-containing *E. coli* cells in a single device. Parallel PCR/CE assays of multiple samples in chips containing multiple reaction wells have also been demonstrated. In addition, competitive immunoassay experiments have been performed on a microchip device that included fluidic elements for mixing of sample with reagents, incubation, and electrophoretic separations. Other microfabricated fluidic elements that have been coupled to electrically driven separations include electrospray ionization for analysis by mass spectrometry, and sample concentration using porous membrane elements and solid phase extraction. Devices have also been demonstrated that employ electrokinetic transport solely for performing chemical and biochemical reactions. Examples include devices for enzymatic reaction kinetics, enzyme assays, organic synthesis, and cellular manipulations. All four of these latter applications could eventually be of significant importance to experimental biology, but have not been sufficiently developed at this time.

A number of microfabricated fluidic devices have also been demonstrated that use hydraulic forces for fluid transport. While the use of hydraulic forces can be applied to a broader range of fluidic materials than electrokinetic phenomena, it is less convenient to implement in general. External connections to microchips for hydraulically driven flow are more cumbersome than applying an electric potential. Moreover, electrokinetically driven forces follow the flow of electrical current and thus, allow greater control over transport within a microchannel manifold versus application of pressure or vacuum to a terminus of such a manifold. Electrokinetic forces are also able to generate much higher effective pressures than is practical with hydraulics. The demonstrated capabilities of hydraulically driven devices appear to be trailing that of electrokinetically driven devices. Nonetheless, a number of important capabilities have been reported.

Microfluidic devices for performing PCR have received considerable interest. Early devices included only chambers machined in silicon to act as sample reservoirs while later devices utilized the silicon structure for resistive heating or utilized integrated filters for the isolation of white blood cells. More recently, an interesting device for continuous flow PCR was reported that utilized a single microchannel that meanders through temperature zones to accomplish thermal cycling. Filters for processing cellular materials have been micromachined into silicon substrates. Flow cytometry devices have also been micromachined into silicon and glass substrates and driven hydraulically.

The capability to manipulate reagents and reaction products "on-chip" suggests the eventual ability to perform virtually any type of "wet-chemical" bench procedure on a microfabricated device. The paradigm shift of moving the laboratory to a microchip includes the advantages of reducing reagent volumes, automation or material manipulation with no moving parts, reduced capital costs, greater parallel processing, and higher processing speed. The volume of fluids that are manipulated or dispensed in the microfluidic structures discussed above is on the nanoliter scale or smaller versus tens of microliters at the laboratory scale, corresponding to a reduction of three orders of magnitude or more. Flow rates on the devices that have been studied are of the order of 1 mL/yr of continuous operation. By implementing multiple processes in a single device (vertical integration), these small fluid quantities can be manipulated from process to process efficiently and automatically under computer control. An operator would only have to load the sample to be analyzed. Obviously, this serial integration of multiple analysis steps can be combined with parallel expansion of processing capacity by replicating microfabricated structures, e.g., parallel separation channels, on the same device.

Although the so-called "Lab-on-a-Chip" appears to hold many promises, and it is believed that it will fulfill many of them, there are further developments necessary to achieve an impact level that parallels the scale of miniaturization realized in the field of microelectronics. There are at least four significant issues that must be addressed to bring "Lab-on-a-Chip" devices to the next level of sophistication, or processing power, over the next decade. Those issues are: advanced microfluidic control, the "world-to-chip" interface, detection, and viable manufacturing strategies. Presently, electrokinetic manipulation of fluids in microchannel structures represents the state-of-the-art in controlled small volume handling with high precision. The strategy has been to control the time-dependent electric potential at each of the channel terminals to move materials along a desired path. While this strategy has been very effective for valving and mixing in simple designs, it is limited in its applicability and performance as designs become more complex. We believe that new strategies that allow control of electric potentials at multiple points in the microchannel design will be necessary for these more complex structures. Electrokinetic transport also has limitations in the types of solutions and materials that can be manipulated.

The world-to-chip interface is the term we have assigned to the problem of delivering multiple samples or reagents onto microchips to achieve high throughput analysis. Although a given sample can be analyzed in times as brief as a millisecond, multiple samples cannot presently be presented to microchip devices at such a rate. There has been very little effort directed toward this problem, but it represents a major hurdle to achieving ultrahigh throughput experimentation.

SUMMARY OF THE INVENTION

In accordance with a first aspect of the present invention, there is provided a method of forming and transporting a series of minute volume segments (nanoliter or subnanoliter) of a material on a fluidic microchip, wherein each of the volume segments are separated by segmenting material. The method includes the steps of providing a first channel having an inlet end connected to a source of transport fluid and an outlet end connected to a fluid reservoir and providing a second channel having an inlet end connected to a source of segmenting fluid and an outlet end interconnected with said first channel. A minute volume of the segmenting fluid is drawn into the first channel and transported in the first channel toward the fluid reservoir. The steps of drawing and transporting the minute volume of segmenting fluid into the first channel are repeated to form a series of transport fluid volumes and/or analysis volumes between the segmenting fluid volumes. Reagents, cells, or reaction beads can be injected or inserted into the transport fluid volumes to provide a series of assay or analysis volumes. The assay or analysis volumes are transported in series fashion so as to provide serial registration thereof for storage and retrieval for later analysis or other manipulation on the microchip.

In accordance with another aspect of this invention, there is provided an apparatus for forming and transporting a series of minute volume segments of a material. The device is a fluidic microchip having first and second microchannels formed on a substrate. The first microchannel has an inlet end connected to a source of transport fluid and an outlet end connected to a fluid reservoir. The second microchannel has an inlet end connected to a source of segmenting fluid and an outlet end interconnected with the first microchannel. A plurality of electrodes are disposed in the first microchannel between the outlet ends of the first microchannel and the second microchannel. A second plurality of electrodes are disposed in said first microchannel between the inlet end of said first microchannel and said second microchannel. The device further includes means for (i) inserting a volume of the segmenting fluid from the second microchannel into the first microchannel, thereby displacing the transport fluid contained in the first microchannel, (ii) stopping the transport of the segmenting fluid volume in the first microchannel, and then (iii) transporting the interleaved transport and segmenting volumes in the first microchannel toward the fluid reservoir.

Further embodiments of the device according to this invention include additional channels, sources of reagents, reagent diluents, cells, and/or reaction particles, for inserting such materials into transport volumes formed by sequential pairs of the segmenting fluid volumes. Means for transporting the reagents, cells, and/or reaction beads are also included in such embodiments. In a preferred arrangement, the first microchannel includes one or more loops to provide serial storage of the reaction volumes for later retrieval and analysis or manipulation.

BRIEF DESCRIPTION OF THE DRAWINGS

The foregoing summary, and the following detailed description, will be better understood when read in conjunction with the attached drawings, in which.

DETAILED DESCRIPTION

Figure 1A:
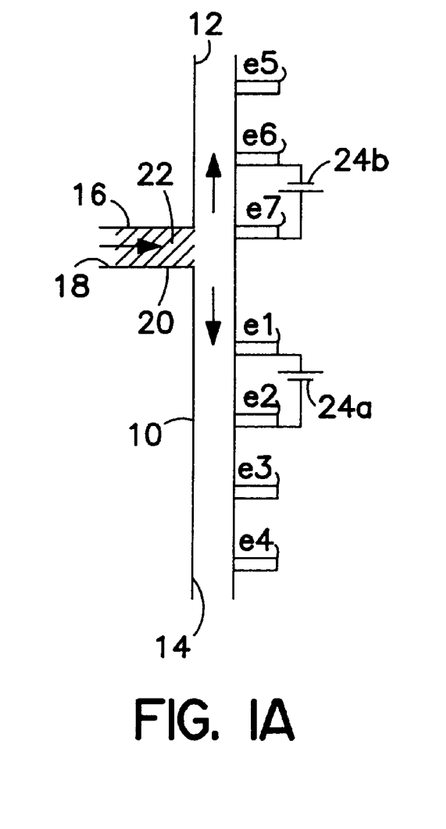
FIGS. 1A, 1B, and 1C are partial schematic diagrams of a microchip showing the sequence of steps in inserting a segmenting fluid volume into a microchannel containing a transport fluid in accordance with one aspect of this invention.
Figure 1B:
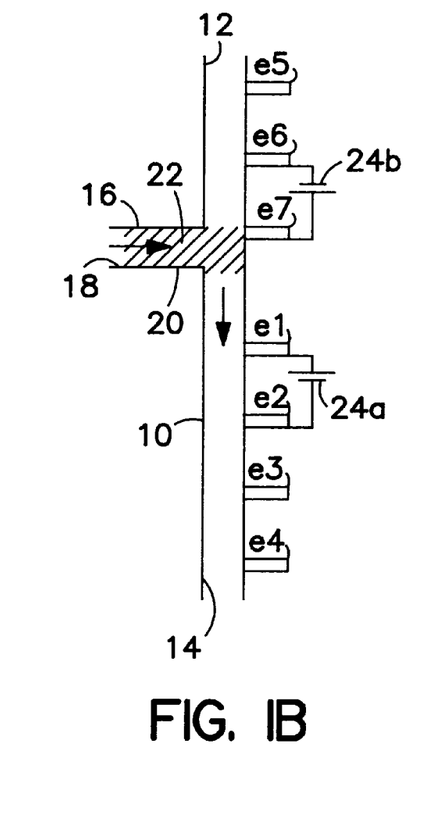
Figure 1C:
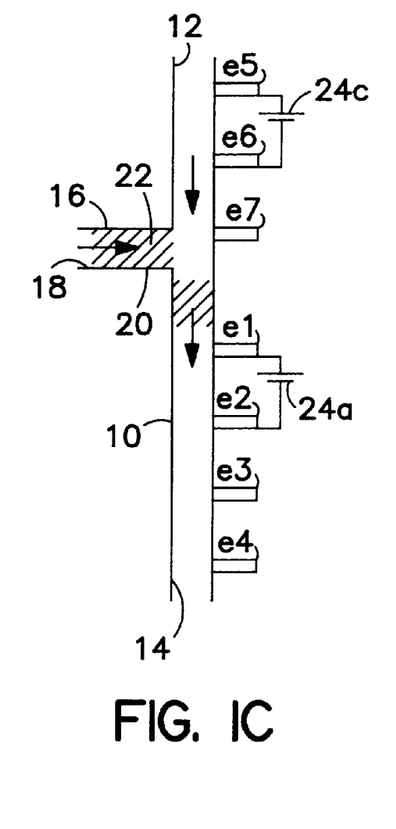

Referring now to the drawings, wherein like reference numerals refer to the same or similar components or features, and in particular to FIGS. 1A, 1B, and 1C, there is shown a main microchannel 10. Main microchannel 10 is substantially linear and has an inlet 12 that is connected to a source of transport fluid (not shown) and an outlet 14 that is connected to a waste reservoir (not shown). A branch channel 16 has an inlet 18 and an outlet 20 that intersects with the main microchannel 10 for conducting a segmenting or isolating fluid 22 into the main channel 10. Electrodes e1, e2, e3, and e4 are disposed at spaced apart locations along main microchannel 10 between outlet 20 and outlet 14. Electrodes e5, e6, and e7 are disposed at spaced apart location along the side of main microchannel between outlet 20 an inlet 12. All electrodes are in contact with fluids contained within the microchannels. Either the transport fluid, the segmenting fluid, or both are transportable through the microchannels when exposed to an axial electric field. This function will be referred to as electrokinetic flow and includes such phenomena as electrophoresis, electroosmosis, and electrohydrodynamic transport.

With the arrangement shown in FIGS. 1A, 1B, and 1C, the segmenting fluid 22 can be inserted into the main microchannel 10 as a series of discrete, minute volumes. The steps for accomplishing the insertion of the minute volumes of the segmenting fluid 22 are essentially as follows. Main microchannel 10 is filled with the transport fluid. A source of electrical potential 24a is applied between electrodes e1 and e2 and a second source of electrical potential 24b is applied between electrodes e6 and e7. The magnitudes and polarities of the electric potentials are selected to induce electrokinetic flow of the transport fluid in main microchannel 10 in the directions indicated by the arrows in FIG. 1A. Such flow of the transport fluid causes the segmenting fluid 22 to be drawn into main microchannel 10 as shown in FIG. 1B. Assuming that the segmenting fluid has a lower conductivity than the transport fluid, when the segmenting fluid 22 comes into contact with electrode e7, the current between electrodes e6 and e7 drops, and fluid flow in that direction ceases. However, the segmenting fluid 22 continues to flow toward the outlet 14 by virtue of the electrical potential across electrodes e1 and e2. When the desired volume of segmenting fluid has been drawn into main microchannel 10, the volume of segmenting fluid is dispensed into main microchannel 10 by applying a source of electric potential 24c between electrodes e5 and e6. The magnitude and polarity of the electric potential between eletrodes e5 and e6 are selected to induce electroosmotic flow of the transport fluid in main microchannel 10 in the directions indicated by the arrows in FIG. 1C. When the volume of segmenting fluid comes into contact with electrode e1, the current between electrodes e1 and e2 drops, and fluid flow in that direction ceases. An electric potential is then applied between electrodes e2 and e3 to continue transporting of the transport fluid and the segmenting fluid volume. Similarly, when the volume of segmenting fluid comes into contact with electrode e2, the current between electrodes e2 and e3 drops, and fluid flow in that direction ceases. An electric potential is then applied between electrode e3 and e4 to further continue the transporting of the transport fluid, and the segmenting fluid volume, along main microchannel 10. The physical construction and operation of a linear pumping arrangement of the type used in the present invention is described in greater detail in our copending patent application Ser. No. 09/244,914 the entire specification of which is incorporated herein by reference.

As an alternative to electrokinetic transport mechanisms, the moving of the transport fluid and the injection of the segmenting fluid, and any other materials used in a device or method according to the present invention can be accomplished by application of pressure or vacuum to the appropriate channel or channels. It is also contemplated that combinations of electrokinetic, pressure, and/or vacuum transport mechanisms can be utilized in implementing a given device or method in accordance with this invention, if desired.

After a segmenting volume has traveled a sufficient distance in main microchannel 10, the process is repeated to insert another segmenting volume. If the pumping rate of the segmenting fluid into the main microchannel 10 is not sufficiently high, then similar electrodes can be placed in branch channel 16.

The segmenting fluid is preferably a liquid that is immiscible in the transport fluid and the reaction fluid(s). Also, the segmenting fluid should be biocompatible with biological reagents that are used. The segmenting fluid is preferably nonconducting for operational control of the reaction/transport process. For example, a nonconducting fluid provides a convenient way to track the location of reaction and pumping volumes in the series of minute volumes transported in the microchannel. Further, the segmenting fluid should have a minimal chemical distribution coefficient for the various reagents that are used. Paraffin and mineral oils are suitable because they have been used to isolate cells in small volumes of extracellular solutions without any deleterious effects. Perfluorocarbons may also be suitable because they are widely used where biocompatibility is required. Silicon oils are yet another suitable class of materials for the segmenting fluid. Gases such as propane may be suitable for use as the segmenting fluid, but could be dissolved into the transport or reaction fluid or escape through a gas-permeable cover plate, thereby reducing their effectiveness for isolating fluid segments.

Following are descriptions of preferred arrangements for implementing various manipulations of minute amounts of materials in serial fashion on a fluidic microchip. Although not shown or described in connection with the various embodiments, the various configurations can include arrangements of electrical contacts as described with reference to FIG. 1 to provide the electric potentials necessary to effectuate the transport of the fluidic materials in the channels of various microfabricated devices. Alternatively, as described above, pressure or vacuum means can also be utilized.

Figure 2:
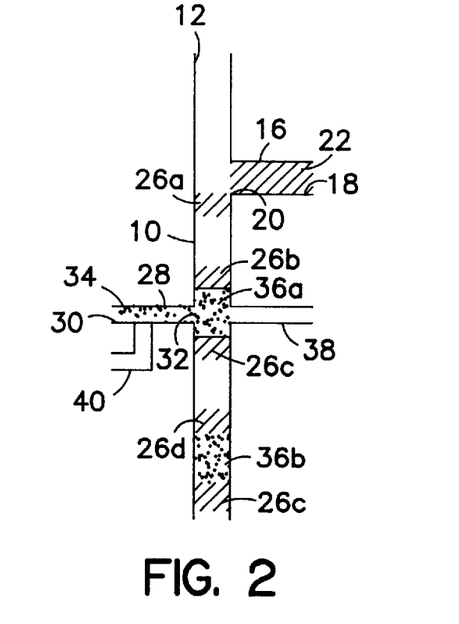
FIG. 2 is a partial schematic diagram of a microchip showing the loading of a reagent into transport volumes between alternating pairs of segmenting fluid volumes in a microchannel in accordance with another aspect of this invention.

A significant feature of the method according to the present invention, is the capability of inserting a series of minute reaction fluid volumes into the series of minute volume segments in the main microchannel. Referring now to FIG. 2, there is shown an arrangement for the controlled loading of reagents into a series of reaction volumes in main microchannel 10. A plurality of segmenting fluid volumes 26a, 26b, 26d, and 26e are inserted into main microchannel 10 at spaced intervals as described above. A reagent channel 28 has an inlet 30 and an outlet 32 that intersects with the main microchannel 10 for conducting a chemical or biochemical reagent 34 into the main microchannel 10. A waste channel 38 interconnects with main microchannel 10 at a location substantially opposite the outlet 32. A diluent channel 40 interconnects with the reagent channel 28 so that a dilution agent can be mixed into the reaction fluid 34. The steps for accomplishing the insertion of minute volumes of the reaction fluid 34 are essentially as follows.

The transport fluid and the segmenting fluid volumes 26a, 26b, 26c, 26d, and 26e are pumped through main microchannel 10. When a sequential pair of segmenting fluid volumes 26b and 26c are adjacent the outlet 32, the pumping is stopped and the reaction fluid 34 is pumped into the volume between segmenting fluid volumes 26b and 26c. The transport fluid contained between the segmenting fluid volumes 26b and 26c is preferably conducted into the waste channel 38. Alternatively, the transport fluid can be added to or replaced. The reaction fluid volume 36a is then transported electrokinetically along main microchannel 10. Although the process according to this aspect of the invention has been described with a static mode of operation, it will be recognized that dynamic transfer of the reaction fluid into the reaction volumes will provide higher throughput. Such dynamic operation could be implemented by controlled transport of the transport fluid and reaction fluid such that the reaction fluid is injected in synchronism with the arrival of a reaction volume at the outlet 32.

Preferably, the reaction fluid volumes 36a and 36b are contained between alternate sequential pairs of segmenting fluid volumes. Thus, as shown in FIG. 2, reaction fluid volume 36a is contained between segmenting fluid volumes 26b and 26c. Whereas, reaction fluid volume 36b is contained between segmenting fluid volumes 26d and 26e. Such alternate sequencing permits the pumping of the reaction fluid volumes through the main microchannel without exposing the reaction fluid to an axial electric field, or in cases where the reaction fluid does not support electrokinetic flow, transport is effected. In other words, the electric potentials are applied only to the segments containing transport fluid. The concentration of the reaction fluid is adjusted by mixing a diluent into the reagent before it is injected into the volume between the segmenting volumes. In this manner, a series of reagent volumes each having a different concentration can be generated.

Figure 3:
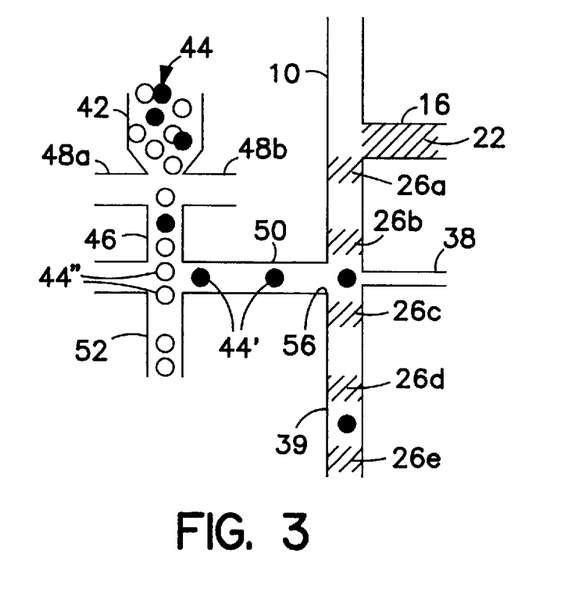
FIG. 3 is a partial schematic diagram of a microchip showing the loading of particles between alternating pairs of segmenting fluid volumes in a microchannel in accordance with another aspect of this invention.

Another significant feature of the method according to the present invention is the capability to insert a series of reaction particles, such as beads or cells, into the series of minute volume segments in the main microchannel. Referring now to FIG. 3 there is shown an arrangement for sorting and loading a plurality of reaction particles 44 into a series of reaction volumes in main microchannel 10. A plurality of segmenting fluid volumes 26a, 26b, 26c, 26d, and 26e are drawn into main microchannel 10 at spaced intervals as described above. A particle reservoir 42 contains a plurality of reaction particles 44 in a suspension fluid. A particle sorting channel 46 is connected to the outlet of the reservoir 42 for receiving the particles 44. A pair of focusing channels 48a and 48b interconnect with the particle sorting channel 44. The focusing channels 48a and 48b provide a focusing fluid to narrow down the flow of particles 44 to a single-particle-width stream. Electrokinetic focusing of this type is described in our co-pending patent application No. 09/098,178, and our issued U.S. Pat. No. 5,858,187, the entire specifications of which are incorporated herein by reference.

A reaction particle channel 50 intersects the particle sorting channel 46 at a location downstream of the focusing channels 48a and 48b. At the intersection of the reaction particle channel 50 and the particle sorting channel 46, the desired reaction particles 44' are separated from the non-desired particles 44". A potential or pressure is applied to the inlet 50a of channel 50 to direct particles 44' into and along channel 50 to the main microchannel 10. Reaction particle channel 50 has an outlet 56 that interconnects with the main microchannel 10 for conducting the reaction particles into the main microchannel 10. The undesired particles 44" are conducted away along a particle waste channel 52 that extends from the particle sorting channel 46.

The steps for accomplishing the insertion of the reaction particles 44' into the transport stream are essentially as follows. The transport fluid and the segmenting fluid volumes 26a, 26b, 26c, 26d, and 26e are pumped electrokinetically through main microchannel 10. When a sequential pair of segmenting fluid volumes 26b and 26c are adjacent the outlet 56, the particle suspension fluid with a single particle is pumped electrokinetically into the volume between segmenting fluid volumes 26b and 26c, and the transport fluid contained therein is conducted into the waste channel 38. In this arrangement, the waste channel cross section, or at least its inlet, is sized to prevent the particle from passing through. The reaction particle and its volume of suspension fluid is then transported electrokinetically along main microchannel 10 to a detection/analysis channel 39. Preferably, the reaction particles are contained between alternate sequential pairs of segmenting fluid volumes. Thus, as shown in FIG. 3, a first particle is contained between segmenting fluid volumes 26b and 26c. Whereas, a second particle is contained between segmenting fluid volumes 26d and 26e. Such alternate sequencing permits the pumping of the reaction fluid volumes through the main microchannel without exposing the reaction particle to an axial electric field. To that end, the electric potentials are applied only to the segments containing transport fluid.

Figure 4:
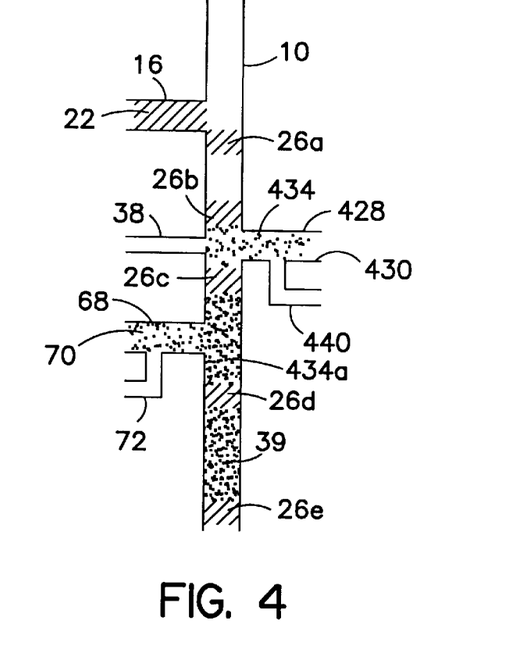
FIG. 4 is a partial schematic diagram of a microchip showing the sequence of inserting a segmenting fluid, an enzyme, and a substrate into a microchannel in series fashion in accordance with a further aspect of this invention.

The ability to precisely manipulate fluid flow and reagent mixing with a fluidic microchip lends itself to the study of enzymatic activity and inhibition thereof. An enzyme assay microchip has important implications for drug discovery and medical diagnostics. Referring to FIG. 4, there is shown an arrangement for providing high throughput enzyme assays. A plurality of segmenting fluid volumes 26a, 26b, 26c, and 26d are inserted into main microchannel 10 at spaced intervals as described previously in this specification. An enzyme channel 428 has an inlet 430 and an outlet that intersects with the main microchannel 10 for conducting a fluidic enzyme material 434 into the main microchannel 10. A waste channel 38 interconnects with main microchannel 10 at a location substantially opposite the outlet of enzyme channel 428. A diluent channel 440 interconnects with the enzyme channel 428 so that a dilution agent can be mixed into the enzyme material 434. A substrate channel 68 has an inlet and an outlet that intersects with the main microchannel 10 downstream of the enzyme channel outlet for conducting a fluidic substrate material 70 into the main microchannel 10. A diluent channel 72 interconnects with the substrate channel 68 so that a dilution agent can be mixed into the substrate material 70.

The steps for accomplishing the insertion of minute volumes of the enzyme material 434 into the main microchannel are essentially the same as those described for injecting the reagent fluids with reference to FIG. 2. The transport fluid and the segmenting fluid volumes 26a, 26b, 26c, 26d, and 26e are pumped through main microchannel 10. When an enzyme volume segment 434a contained between a sequential pair of segmenting fluid volumes 26b and 26c is adjacent the outlet of substrate channel 68, the pumping is stopped and the fluidic substrate material 70 is pumped into the enzyme volume segment 434a. The enzyme material and the substrate are mixed in the reaction volume. The combined fluid volume is then transported along main microchannel 10 to a detection/analysis channel 39. The concentrations of the enzyme and substrate materials can be varied by varying the amount of diluent mixed into each one, thereby producing a multitude of different enzyme assays which can be transported along the microchannel 10 in serial fashion.

Means for adding an inhibitor to the reaction volume can also be provided. In one embodiment of such a process, a bead shift register is implemented for delivery of the inhibitors. In such an arrangement, the enzyme, substrate, and inhibitor will be reacted, and the location of the bead leading to positive inhibition is recorded for future analysis. An alternative arrangement is to pool a bead library into a reservoir from which the beads are randomly dispensed. Individual beads are transported to a location where a compound is delivered to a reaction volume containing an assay target. The bead is indexed in a shift register arrangement such as that shown and described with reference to FIG. 3, but only for a time sufficient to give an assay result. If the result is negative, the bead is transferred into a general storage reservoir, but if inhibition is observed, the bead is stored in the shift register for either immediate or later identification of the compound, e.g., by electrospray mass spectrometry.

The enzyme activity of the reaction volume is analyzed with appropriate instrumentation in the analysis channel 39 which is located at an appropriate distance downstream from microchannel 10. The actual distance depends on the required incubation time of the enzyme, substrate, and inhibitor, and the average linear velocity of the assay reaction volume.

In one example of an enzyme assay using electrokinetic mixing and transport of reagents on a fluidic microchip in accordance with this embodiment of the present invention, a fluorogenic substrate (resorufin-$\beta$-D-galactopyranoside) is mixed with the enzyme $\beta$-galactosidase. The kinetics of the reaction are obtained by monitoring the fluorescence of the hydrolysis product, resorufin. Michaelis-Menten constants are derived for the hydrolysis reaction in the presence and absence of inhibitors. A second example of an enzyme assay that can be implemented in the method according to the present invention, is an assay for determining acetylcholinesterase (AchE) activity. This is to stage assay whereby the AchE hydrolyzes acetylthiocholine ti thioline which in turn reacts with coumarinylphenylmaleimide (CPM) to produce a highly fluorescent thioether, CPM thiocholine. The fluorescence of the latter product is monitored to determine the enzyme activity. The presence of an inhibitor would reduce the fluorescence signal relative to the absence of such inhibitor.

Figure 5:
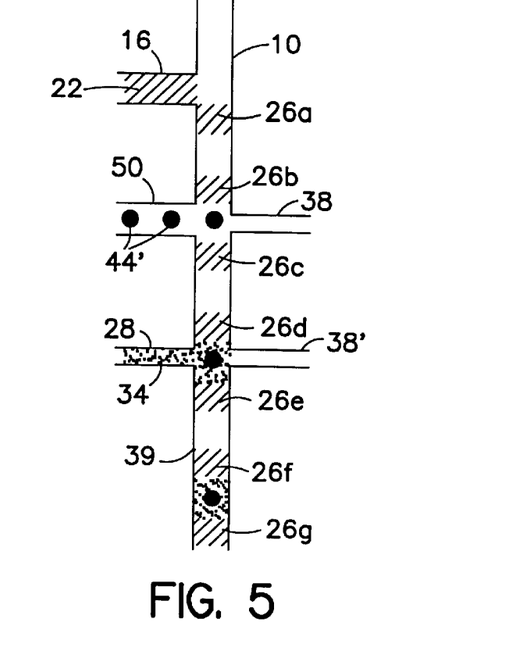
FIG. 5 is a partial schematic diagram of a microchip showing the sequence of inserting a segmenting fluid, a reaction particle, and a reagent fluid into a microchannel in series fashion in accordance with a still further aspect of this invention.

Shown in FIG. 5 is an arrangement for high throughput screening for cellular assays including cell viability. A plurality of segmenting fluid volumes 26a–26g are inserted into main microchannel 10 at spaced intervals from the branch channel 16 as described above. A cell channel 50 intersects the main microchannel 10 for conducting the cells 44' into the main microchannel 10 at a location downstream of the branch channel 16. The cells are suspended in a biocompatible buffer. A waste channel 38 interconnects with main microchannel 10 at a location substantially opposite the outlet of cell channel 50. The cross section of waste channel 38 is dimensioned to be smaller than the minimum major cross-sectional dimension of the cells 44'. A reagent channel 28 intersects the main microchannel 10 at a location downstream of the cell channel 50. A second waste channel 38' interconnects with main microchannel 10 at a location substantially opposite the outlet of reagent channel 28.

The transport fluid and the segmenting fluid volumes 26a–26g are pumped through main microchannel 10. When a sequential pair of segmenting fluid volumes 26b and 26c are adjacent to the outlet of cell channel 50, the cell suspension fluid is pumped into the reaction volume between segmenting fluid volumes 26b and 26c so that a single cell is inserted into the reaction volume. Alternatively, an ensemble of cells could be loaded into a reaction volume. Concurrently, the transport fluid contained therein is conducted into the waste channel 38. The cell and its volume of suspension fluid in the reaction volume is then transported along main microchannel 10 to the outlet of reagent channel 28. The reagent 34 is pumped into the reaction volume containing the cell, displacing the cell suspension fluid. The cell suspension fluid is conducted away through waste channel 38'. The cell and reagent in the reaction volume are then transported to the detection/analysis channel 39. This process is repeated for each cell. Preferably, the cells 44' are contained in reaction volumes between alternate sequential pairs of segmenting fluid volumes as previously described herein. Cellular assays are examined as a function of time, pumping conditions, and media composition.

Figure 6:
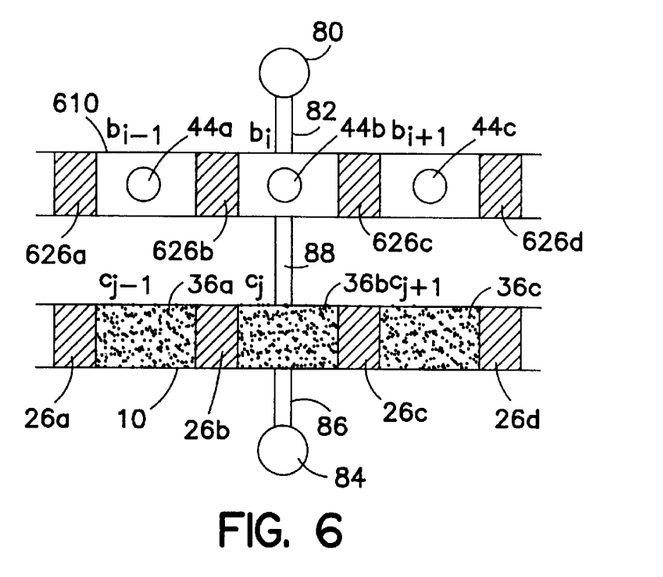
FIG. 6 is a partial schematic diagram of a microchip showing an arrangement for preparing a series of enzyme-bead assays.

The extremely low consumption of reagent materials in microfluidic chips provides a significant advantage for screening expensive reagent and inhibitor materials and their substrate materials. Peptide libraries for such experiments can be custom synthesized on 10 to 100 micron diameter or larger beads with orthogonal releasable linkers. Shown in FIG. 6 is a basic arrangement for implementing a bead screening procedure on a fluidic microchip in accordance with the present invention. A pair of microchannels 10 and 610 are arranged in spaced parallel relation. A buffer reservoir 80 is connected to the microchannel 610 through a buffer channel 82. A waste reservoir 84 is connected to the microchannel 10 through a waste channel 86. A transfer channel 88 interconnects the microchannel 610 to the microchannel 10 at a location substantially in alignment with the buffer channel 82 and the waste channel 86.

A series of reaction volumes are formed between segmenting fluid volumes 26a–26d in microchannel 10 and a corresponding series of reaction volumes are formed between segmenting fluid volumes 626a–626d in microchannel 610. The reaction volumes in each microchannel are transported along the respective microchannels such that reaction volumes $b_{i-1}$, $b_i$, and $b_{i+1}$ in microchannel 610 are maintained in synchronism with reaction volumes $c_{j-1}$, $c_j$, and $c_{j+1}$ in microchannel 10. Beads 44a, 44b, and 44c are inserted in the reaction volumes $b_{i-1}$, $b_i$, and $b_{i+1}$, respectively, in a manner similar to that described above with reference to FIG. 3. Enzyme volumes 36a, 36b, and 36c are inserted in the reaction volumes $c_{j-1}$, $c_j$, and $c_{j+1}$, respectively, in a manner similar to that described above with reference to FIG. 2.

When each bead arrives at the transfer channel 88, its compound is released from the bead and transferred to the corresponding reaction volume. The bead and its associated reaction volume are then shifted in registration to a downstream station where a fluorogenic substrate is added to the reaction volume ($c_{j-1}$, $c_j$, and $c_{j+1}$) for fluorescence assay. A bead corresponding to a reaction volume that exhibits inhibition can be sorted out and transferred to a station where a second release of compound is effected by an orthogonal cleavage method. That compound can be analyzed by electrospray ionization mass spectrometry to determine its chemical structure.

Figure 7:
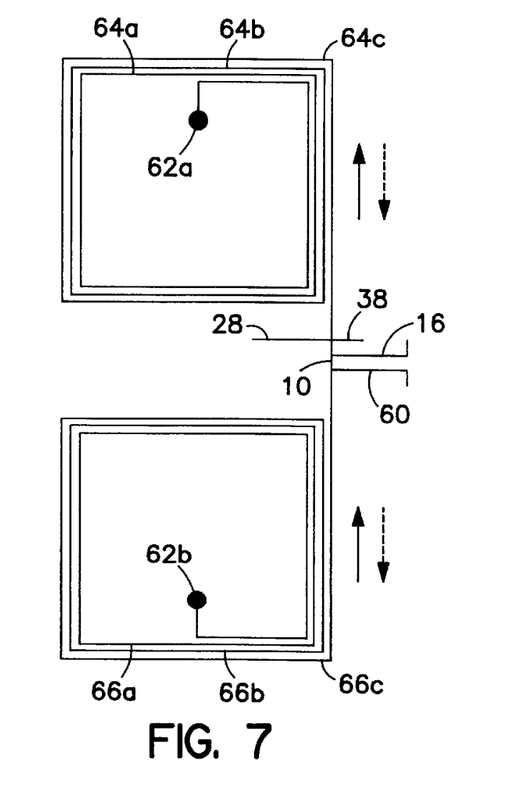
FIG. 7 is a schematic diagram of a microchip showing a arrangement for storing and retrieving a series of cells, reaction beads, or reagent volumes.

The utilization of any of the fluidic microchip-implemented procedures described above yields an extended series of discrete assays, cells, beads, etc. transported in a microchannel. The reaction volumes involved are preferably nanoliter or sub-nanoliter volumes, thus providing numerous different compounds, assays, cells, beads, etc. It is also contemplated that larger volumes can be used. Since each reaction volume is discrete, its position can be identified and tracked as it moves through the microchannel, analogous to a series of electronic bits moving through a digital shift register. Shown in FIG. 7 is an arrangement for archiving and retrieving numerous reaction volumes containing reagents, cells, combinational library beads, etc. A microchannel 10 is connected to a source of transport fluid through a transport fluid channel 60. As described previously, a segmenting fluid is provided to the microchannel 10 through a branch channel 16. Reagents, cells, or beads are inserted into the reaction volumes in microchannel 10 through reagent channel 28. A waste channel 38 is interconnected with microchannel 10 for conducting away the transport fluid from the reaction volume.

The microchannel 10 extends in one direction to form a plurality of loops 64a, 64b, and 64c and terminates in a reservoir 62a. Microchannel 10 extends in an opposite direction to form a second plurality of loops 66a, 66b, and 66c, and terminates in a reservoir 62b. In a first mode of operation, the reaction volumes formed between the segmenting fluid volumes are advanced by transporting them in step-wise fashion in the direction shown by the solid arrows and through loops 64a, 64b, and 64c for archiving. In a second mode of operation, the reaction volumes are retrieved by transporting them in step-wise fashion in the direction shown by the dashed arrows. The combined length of loops 66a, 66b, and 66c is similar in length to the combined length of loops 64a, 64b, and 64c, so that the entire series of reaction volumes archived in loops 64a, 64b, and 64c can be retrieved for later analysis.

Although not shown in FIG. 7, the electrode layout needed to implement the archiving/retrieval device for method 1 would be such as to enable the transport of the reaction volumes in two directions. Preferably, the electrodes or contacts would enter from each of the four sides of the loops. The electrodes geometry is selected to provide adequate contact with the microchannel loops at a proper spatial periodicity. With such a layout, materials can be loaded serially into the register to be analyzed immediately or at a later time. The materials can be delivered to reagent or assay stations as the reaction volumes are shifted back and forth between the microchannel loops.

The number of reaction volumes that can be held in the storage bank defined by loops 64a, 64b, and 64c can be estimated using Equation 1 below.

$$N = \frac{4L_S}{(L_R + L_I)}\left(n - \frac{n(2n-1)}{2}\frac{L_c}{L_S}\right) \quad \{Eq. 1\}$$

$L_S$ is the length of one side of the outermost loop, $L_R$ is the length of the reaction volume, $L_I$ is the length of the isolating segment, $L_C$ is the center-to-center spacing between adjacent channels in the loops, and n is the number of loops. For example, if $L_S$ is 100 mm, $L_R+L_I=1$ mm, $L_C$ is 0.1 mm, and n=100, then approximately 19010 reaction volumes (N) can be stored in the shift register storage loops. Such a device would use only about 10% of the area of a 100 mm×100 mm square microchip substrate. Although the preferred arrangement described herein includes one or more loops to form the storage channel, it will be readily appreciated by those skilled in the art that other configurations can be utilized. For example, a serpentine arrangement would be equally effective.

Such shift register storage/retrieval devices are very advantageous for handling combinatorial bead libraries as described with reference to FIGS. 5 and 6. Beads from a split-synthesis could be collectively loaded into a reservoir and dispensed, using on-chip bead sorting capabilities, into the storage register. Compounds can be partially photolytically released from the beads as needed or prereleased into the contents of the reaction volume. The bead library can be certified by incorporating an electrospray ionization station on the microchip for mass spectrometric identification of the reaction compounds. Beads can also be brought to a location where the compound is delivered to a separate reaction volume to perform a biological assay as described with reference to FIG. 6.

Figure 8:
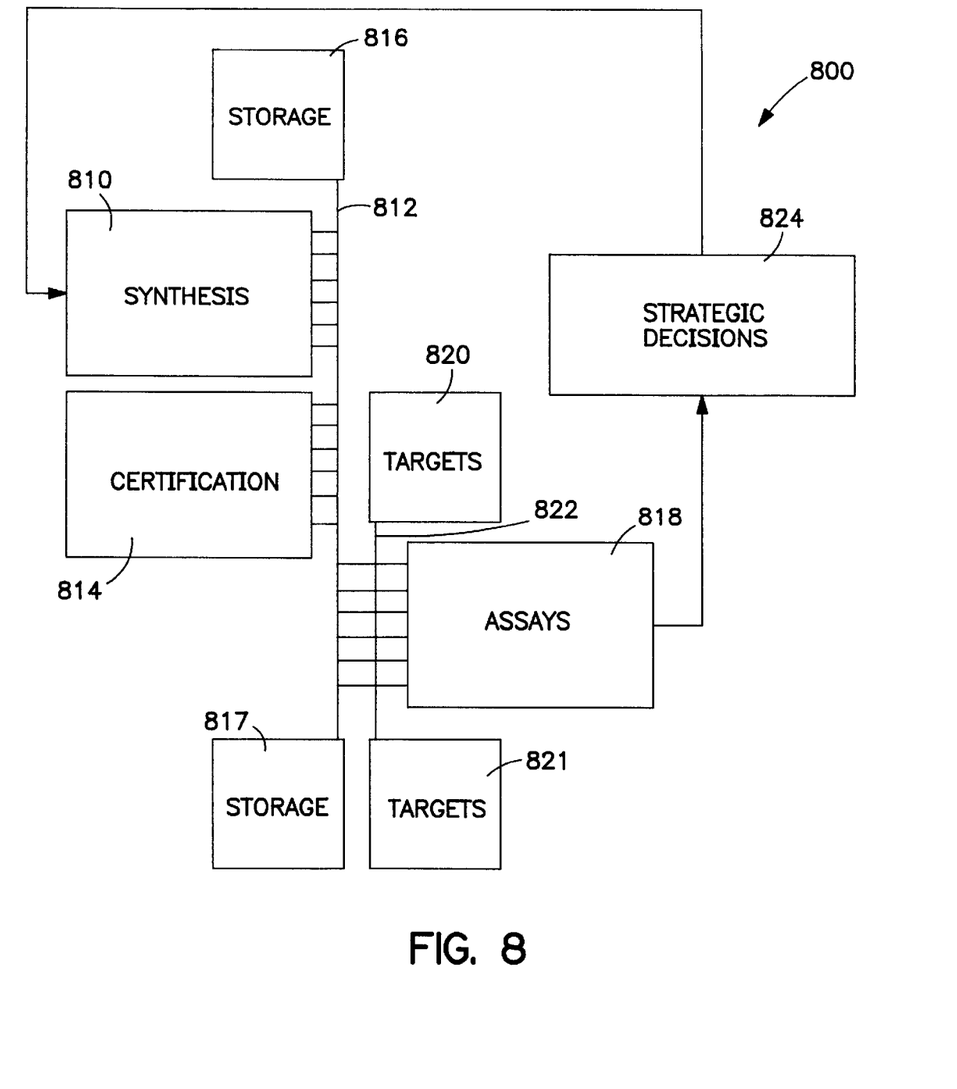
FIG. 8 is a schematic of a system for investigating and identifying new drugs which incorporates a microchip as shown in FIG. 7.

Referring now to FIG. 8, there is shown a system 800 for accomplishing the identification of new drugs. A synthesis module 810 for synthesizing a series of potentially useful drug compounds is connected to a main microchannel 812 through a plurality of insertion channels. Each of the synthesized compounds is inserted into a transport volume and transported along microchannel 812 in the manner described previously hereinabove. A certification module 814 is provided for analyzing and certifying the molecular structure of the synthesized compounds. The certification module is connected to the microchannel 812 through a second plurality of channels for obtaining samples of the synthesized compounds. An assay module 818 for performing screening assays on the series of synthesized compounds against molecular or cellular targets is also provided. Screening module 818 is connected to the microchannel 812 by a third plurality of channels for obtaining samples of the synthesized drug compounds. The target molecules or cells are stored in serial fashion in the target storage modules 820, 821. A second microchannel 822 is disposed between the target storage modules for transporting the targets to the screening module 818.

The series of drug compounds are transported along microchannel 812 to storage modules 816, 817 for later retrieval. This feature permits the drug compounds to be analyzed and/or screened at a time substantially later than the time of synthesis. The results of the screenings performed by the screening module 818 are provided to a decision module 824 which can evaluate the effectiveness of the synthesized compounds and provide feedback to the synthesis module 810 for synthesizing new and different compounds based on the earlier results. In this manner a multitude of new drug compounds can be rapidly and automatically synthesized, certified, and screened on a single microchip.

In view of the foregoing descriptions and the accompanying drawings, it will be appreciated by those skilled in the art that the method and apparatus according to this invention are capable of addressing a broad range of biochemical analysis problems that benefit from precise and automated nanoliter or subnanoliter scale manipulations with high serial throughput capacity. The device and method described herein also lend themselves to multiple parallel expansion which will provide greater throughput for the generation of chemical and biochemical information. The microchannel devices described can manipulate biochemical reaction volumes in a controlled manner to provide rapid results, e.g., rates of at least about 1 to 10 Hz per channel, and rates up to 100 Hz or 1000 Hz are expected to be achievable. The reaction volumes utilized are capable of containing molecular or particulate species without diffusive losses.

The individual reaction volumes are manipulated in serial fashion analogous to a digital shift register. The device includes looped microchannels to provide serial storage of the reaction volumes for later retrieval. The method and apparatus according to this invention have application to such problems as screening molecular or cellular targets using single beads from split-synthesis combinatorial libraries, screening single cells for RNA or protein expression, genetic diagnostic screening at the single cell level, or performing single cell signal transduction studies.

The terms and expressions which have been employed in the foregoing description are used as terms of description and not of limitation. There is no intention in the use of such terms and expressions of excluding any equivalents of the features shown and described or portions thereof It is recognized, however, that various modifications such as channel dimension, location, and arrangement are possible within the scope of the invention as claimed.

What is claimed is:

1. A method of forming and transporting a series of minute volume segments of a material in a microchannel comprising the steps of:
   a. providing a microchannel device having a first channel having an inlet end connected to a source of transport liquid and an outlet end and having a second channel having an inlet end connected to a source of segmenting liquid that is immiscible with the transport liquid and an outlet end interconnected with said first channel;
   b. drawing a volume of segmenting liquid into said first channel through said second channel;
   c. transporting the volume of segmenting liquid in said first channel toward said first channel outlet end; and then
   d. repeating steps b. and c. to form a series of discrete volumes of the segmenting liquid.

2. A method as set forth in claim 1 wherein the microchannel device comprises first, second, and third electrical contacts in said first channel at a location between the outlet ends of said first channel and said second channel, and fourth, fifth, and sixth electrical contacts in said first channel at a location between the inlet end of said first channel and the outlet end of said second channel; and
   wherein the step of drawing the volume of the segmenting liquid into the first channel comprises applying a first electrical potential across said first and second electrical contacts and a second electrical potential across said fourth and fifth electrical contacts, said first and second electrical potentials having magnitudes and polarities that are effective for inducing flow of said transport liquid in said first channel so as to draw the segmenting liquid into said first channel.

3. A method as set forth in claim 2 comprising the steps of:
   a. reducing the magnitude of the second electrical potential across said fourth and fifth electrical contacts; and
   b. maintaining the magnitude and polarity of the first electrical potential across said first and second electrical contacts until the desired volume of segmenting liquid has been drawn into the first channel.

4. A method as set forth in claim 3, wherein the step of transporting the volume of segmenting liquid in said first channel comprises the steps of:
   a. applying a third electrical potential across said fifth and sixth electrical contacts while maintaining the first electrical potential across said first and second electrical contacts until the volume of segmenting liquid reaches said first electrical contact; and then
   b. applying a fourth electrical potential across the second and third electrical contacts, whereby the volume of segmenting liquid is transported toward the second electrical contact.

5. A method as set forth in claim 1 comprising the step of inserting a volume of at least one reagent into said first channel between a sequential pair of the segmenting liquid volumes.

6. A method as set forth in claim 5 wherein the microchannel device comprises a third channel having an inlet end connected to a source of reagent and an outlet end interconnected with the first channel, and a fourth channel having an inlet end interconnected with the first channel; and
   wherein the step of inserting the reagent comprises applying a motive force to cause the volume of the reagent to flow into said first channel and the transport liquid to flow into said fourth channel.

7. A method as set forth in claim 6 wherein the motive force comprises an electrokinetic force.

8. A method as set forth in claim 6 wherein the motive force is selected from the group consisting of vacuum, pressure, an electrical potential, and combinations thereof.

9. A method as set forth in claim 5 comprising the step of diluting the concentration of the reagent before it is inserted into the first channel.

10. A method as set forth in claim 5 comprising the step of repeating the inserting of the reagent into the first channel such that a plurality of volumes of reagent are inserted between non-adjacent, sequential pairs of volumes of the segmenting liquid.

11. A method as set forth in claim 10 comprising the step of transporting the plurality of inserted volumes of reagent along said first channel toward said first channel outlet end.

12. A method as set forth in claim 11 comprising the step of sequentially storing the plurality of inserted volumes of reagent so that a selected one of said reagent volumes can be retrieved.

13. A method as set forth in claim 12 comprising the step of retrieving the selected reagent volume from storage.

14. A method as set forth in claim 5 wherein the microchannel device comprises a third channel having an inlet end connected to a source of reagent and an outlet end interconnected with the first channel and wherein the step of inserting the reagent comprises applying a motive force to cause the volume of the reagent to flow into said first channel.

15. A method as set forth in claim 14 wherein the motive force is selected from the group consisting of vacuum, pressure, an electrical potential, and combinations thereof.

16. A method as set forth in claim 5 comprising the step of repeating the inserting of the reagent into the first channel such that a plurality of volumes of reagent are inserted between pairs of volumes of the segmenting liquid.

17. A method as set forth in claim 5 comprising the step of inserting a volume of a second reagent, a cell, a diluent, or a particle into said first channel, between the sequential pair of segmenting fluid volumes.

18. A method as set forth in claim 1 comprising the step of inserting a particle into said first channel between a sequential pair of the volumes of the segmenting liquid.

19. A method as set forth in claim 18 comprising the step of repeating the insertion of the particle into the first channel such that a plurality of particles are inserted between non-adjacent, sequential pairs of volumes of the segmenting liquid.

20. A method as set forth in claim 19 comprising the step of transporting the plurality of particles along said first channel toward said first channel outlet end.

21. A method as set forth in claim 18 comprising the step of repeating the insertion of a particle into the first channel such that a plurality of particles are inserted between pairs of volumes of the segmenting liquid.

22. A method as set forth in claim 1 comprising the step of drawing a volume of the transport liquid into said first channel after each iteration of step c., whereby alternating discrete volumes of segmenting liquid and transport liquid are created in said first channel.

23. A method of forming and transporting a series of minute volume segments of a material in a microchannel comprising the steps of;
   a. providing a microchannel device having a first channel having an inlet end connected to a source of transport fluid and an outlet end and having a second channel having an inlet end connected to a source of segmenting fluid and an outlet end interconnected with said first channel;
   b. drawing a volume of segmenting fluid into said first channel through said second channel;
   c. transporting the volume of segmenting fluid in said first channel toward said first channel outlet end;
   d. repeating steps b. and c. to form a series of discrete volumes of the segmenting fluid;
   e. inserting a particle into said first channel between a sequential pair of the volumes of the segmenting fluid;
   f. repeating the insertion of the particle into the first channel such that a plurality of particles are inserted between non-adjacent, sequential pairs of volumes of the segmenting fluid;
   g. transporting the plurality of particles along said first channel toward said first channel outlet end; and
   h. sequentially storing the plurality of inserted particles so that a selected one of said particles can be retrieved.

24. A method as set forth in claim 23 comprising the step of retrieving the selected particle from storage.

25. An apparatus for forming and transporting a series of minute volume segments of a material comprising:
   a substrate having first and second microchannels formed therein, said first microchannel having an inlet end connected to a source of transporter fluid and an outlet end, said second microchannel having an inlet end connected to a source of segmenting fluid and an outlet end interconnected with said first microchannel;
   first, second, and third electrical contacts disposed in said first microchannel at a location intermediate the outlet end of said first microchannel and second microchannel;
   fourth, fifth, and sixth electrical contacts disposed in said first microchannel at a position intermediate tie inlet end of said flat microchannel and said second microchannel; and
   means for sequentially applying electrical potentials across adjacent pairs of said electrical contacts to (i) draw a volume of the segmenting fluid into said first microchannel, (ii) stop the drawing of the segmenting fluid volume in the first microchannel, and then (iii) transport the volumes of the segmenting fluid in said first microchannel toward said first channel outlet end,
   wherein said electrical contacts are adapted to sense electrical contact with the segmenting fluid volume.

26. Apparatus as set forth in claim 25 comprising:
   a third channel having an inlet end connected to a source of reagent and an outlet end interconnected with the first channel; and
   means for inserting a volume of the reagent between a pair of sequential volumes of the segmenting fluid in said first channel.

27. Apparatus as set forth in claim 26 comprising a fourth channel having an inlet end interconnected with the first channel and means for applying an electrical potential between the fourth channel and the third channel for inserting the volume of the reagent, such that the transport fluid disposed between said pair of segmenting fluid volumes is caused to flow into said fourth channel.

28. Apparatus as set forth in claim 26 comprising means for diluting the reagent when it is inserted into the first channel.

29. Apparatus as set forth in claim 26 comprising:
   additional electrical contacts located along the first channel between the third channel and the first channel outlet end; and
   means for applying electrical potentials between respective pairs of the additional electrical contacts for transporting the reagent volume along said first channel toward said first channel outlet end.

30. Apparatus as set forth in claim 26 comprising means for inserting, between the pair of sequential volumes of the segmenting fluid, a material selected from the group consisting of a volume of a second reagent, a cell, a particle, and a diluent.

31. Apparatus as set forth in claim 25 comprising:
   a third channel having an inlet end connected to a source of particles suspended in a fluid medium and an outlet end interconnected with the first channel; and
   means for inserting a particle suspended in the fluid medium between a pair of sequential volumes of the segmenting fluid in said first channel.

32. Apparatus as set forth in claim 31 comprising a fourth channel having an inlet end interconnected with the first channel and means for applying an electrical potential between the fourth channel and the third channel to cause a volume of the fluid medium containing the particle to flow into said first channel and the transport fluid to flow into said fourth channel.

33. Apparatus as set forth in claim 31 comprising means for selecting the particles from the source of particles according to a quality or characteristic of the particle and means for inserting the selected particle between a pair of sequential segmenting fluid volumes.

34. Apparatus as set forth in claim 31 comprising means for controlling the insertion of each of the particles such that the particles are inserted between pairs of the segmenting fluid volumes in said first channel.

35. Apparatus as set forth in claim 31 comprising:

additional electrical contacts located along the first channel between the third channel and the first channel outlet end; and means for applying electrical potentials respective pairs of the additional electrical contacts for transporting the segmenting fluid volume along said first channel toward said first channel outlet end.

36. An apparatus for forming and transporting a series of minute volume segments of a material comprising:

a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;

first, second, and third electrical contacts disposed in said first microchannel at a location intermediate the outlet end of said fist microchannel and said second microchannel;

fourth, fifth, and sixth electrical contacts disposed in said first microchannel at a position intermediate the inlet end of said first microchannel and said second microchannel;

means for sequentially applying electrical potentials across adjacent pairs of said electrical contacts to (i) draw a volume of the segmenting fluid into said first microchannel, (ii) stop the drawing of the segmenting fluid volume in the first microchannel, and then (iii) transport the volumes of the segmenting fluid in said first microchannel toward said first channel outlet end;

a third channel having an inlet end connected to a source of reagent and an outlet end interconnected with the first channel;

means for inserting a volume of the reagent between a pair of sequential volumes of the segmenting fluid in said first channel; and means for varying the dilution of the reagent to provide a series of volumes of diluted reagent having different concentrations and means for inserting each of the diluted volumes between pairs of the segmenting fluid volumes in said first channel.

37. Apparatus as set forth in claim 36 wherein said first channel comprises a loop for holding a plurality of said diluted reagent volumes disposed between the pairs of the segmenting fluid volumes.

38. Apparatus as set forth in any one of claims 28, 29, 36 and 37 comprising a fourth channel having an inlet end interconnected with the first channel.

39. An apparatus for forming and transporting a series of minute volume segments of a material comprising:

a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;

first, second, and t electrical contacts disposed in said first microchannel at a location intermediate the outlet end of said first microchannel and said second microchannel;

fourth, fifth, and sixth electrical contacts disposed in said first microchannel at a position intermediate the inlet end of said first microchannel and said second microchannel;

means for sequentially applying electrical potentials across adjacent pairs of said electrical contacts to (i) draw a volume of the segmenting fluid into said first microchannel, (ii) stop the drawing of the segmenting fluid volume in the first microchannel, and then (iii) transport the volumes of the segmenting fluid in said first microchannel toward said first channel outlet end;

a third channel having an inlet end connected to a source of particles suspended in a fluid medium and an outlet end interconnected with the first channel; and means for inserting a particle suspended in the fluid medium between a pair of sequential volumes of the segmenting fluid in said first channel, wherein said fist channel comprises a loop for holding a plurality of said particles disposed between pairs of the segmenting fluid volumes.

40. An apparatus for forming and transporting a series of minute volume segments of a material comprising:

a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;

means for sequentially applying a motive force to (i) draw a volume of the segmenting fluid into said first microchannel, (ii) stop the drawing of the segmenting fluid volume in the first microchannel, and then (iii) transport the volume of the segmenting fluid in said first microchannel toward said first channel outlet end; and at least two electrical contacts disposed at said first microchannel and adapted to sense the presence of the segmenting fluid volume.

41. Apparatus as set forth in claim 40 comprising:

a third channel having an inlet end connected to a source of reagent and an outlet end interconnected with the first channel, and means for inserting a volume of the reagent between a pair of sequential volumes of the segmenting fluid in said first channel.

42. Apparatus as set forth in claim 41 comprising a fourth channel having an inlet end interconnected with the first channel and comprising means for applying a motive force between the fourth channel and the third channel for inserting the volume of the reagent such that the transport fluid disposed between said pair of sequential volumes of the segmenting fluid is caused to flow into said fourth channel.

43. Apparatus as set forth in claim 41 comprising means for diluting the reagent when it is inserted into the first channel.

44. Apparatus as set forth in claim 41 comprising means for inserting, between the pair of sequential volumes of the segmenting fluid, a volume of a second material selected from the group consisting of a reagent, a cell, a particle, and a diluent.

45. Apparatus as set forth in claim 40 comprising a third channel having an inlet end connected to a source of particles suspended in a fluid medium and an outlet end interconnected with the first channel, and means for inserting a particle between a pair of sequential volumes of the segmenting fluid in said first channel.

46. Apparatus as set forth in claim 45 comprising means for selecting the particles according to a quality or characteristic of the particles and means for inserting selected particles between a pair of sequential volumes of the segmenting fluid in said first channel.

47. Apparatus as set forth in claim 45 comprising means for controlling the insertion of each of the particles such that the particles are inserted between pairs of the segmenting fluid volumes in said first channel.

48. Apparatus as set forth in claim 45 comprising a fourth channel having an inlet end interconnected with the first channel and comprising means for applying a motive force between the fourth channel and the third channel to cause a volume of the fluid medium containing the particle to flow into said first channel and the transport fluid to flow into said fourth channel.

49. Apparatus as set forth in claim 45 comprising means for inserting between the pair of sequential volumes of the segmenting fluid, a volume of a second material selected from the group consisting of a reagent, a cell, a particle, and a diluent.

50. An apparatus for forming and transporting a series of minute volume segments of a material comprising:
   a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;
   means for sequentially applying a motive force to (i) draw a volume of the segmenting fluid into said first microchannel, (ii) stop the drawing of the segmenting fluid volume in the first microchannel, and then (iii) transport the volume of the segmenting fluid in said first microchannel toward said first channel outlet end;
   a third channel having an inlet end connected to a source of reagent and an outlet end interconnected with the first channel;
   means for inserting a volume of the reagent between a pair of sequential volumes of the segmenting fluid in said first channel; and
   means for varying the dilution of the reagent to provide a series of volumes of diluted reagent having different concentrations and means for inserting each of the diluted volumes into pairs of the segmenting fluid volumes in said first channel.

51. An apparatus for forming and transporting a series of minute volume segments of a material comprising:
   a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;
   means for sequentially applying a motive force to (i) draw a volume of the segmenting fluid into said first microchannel, (ii) stop the drawing of the segmenting fluid volume in the first microchannel, and then (iii) transport the volume of the segmenting fluid in said first microchannel toward said first channel outlet end;
   a third channel having an inlet end connected to a source of reagent and an outlet end interconnected with the first channel; and
   means for inserting a volume of the reagent between a pair of sequential volumes of the segmenting fluid in said first channel,
   wherein said first channel comprises a loop for holding a plurality of said reagent volumes disposed between pairs of the segmenting fluid volumes.

52. An apparatus for forming and transporting a series of minute volume segments of a material comprising:
   a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;
   means for sequentially applying a motive force to (i) draw a volume of the segmenting fluid into said first microchannel, (ii) stop the drawing of the segmenting fluid volume in the first microchannel, and then (iii) transport the volume of the segmenting fluid in said first microchannel toward said first channel outlet end;
   a third channel having an inlet end connected to a source of particles suspended in a fluid medium and an outlet end interconnected with the first channel, and
   means for inserting a particle between a pair of sequential volumes of the segmenting fluid in said first channel,
   wherein said first channel comprises a loop for holding a plurality of said particles disposed between pairs of the segmenting fluid volumes.

53. An apparatus for forming and transporting a series of minute volume segments of a material comprising:
   a substrate having first and second microchannels formed therein, said first microchannel having an inlet end connected to a source of transport fluid and an outlet end, said second microchannel having an inlet end connected to a source of segmenting fluid and an outlet end interconnected with said first microchannel;
   means for sequentially applying a motive force to (i) draw a volume of the segmenting fluid into said first microchannel, (ii) stop the drawing of the segmenting fluid volume in the first microchannel, and then (iii) transport the volume of the segmenting fluid in said first microchannel toward said first channel outlet end;
   a third channel having an inlet end connected to a source of particles, comprising a cell or a bead, suspended in a fluid medium and an outlet end interconnected with the first channel; and
   means for inserting a particle between a pair of sequential volumes of the segmenting fluid in said first channel.

54. A method of forming and transporting a series of minute volume segments of a material in a microchannel comprising the steps of:
   a. providing a microchannel device having a first channel having an inlet end connected to a source of transport fluid and an outlet end and having a second channel having an inlet end connected to a source of segmenting fluid and an outlet end interconnected with said first channel;
   b. drawing a volume of segmenting fluid into said first channel through said second channel;
   c. transporting the volume of segmenting fluid in said first channel toward said first channel outlet end;
   d. repeating steps b. and c. to form a series of discrete volumes of the segmenting fluid; and
   e. sensing the presence of the segmenting fluid volume within said first channel.

55. An apparatus for forming and transporting a series of minute volume segments of a material comprising:
   a substrate having
      first and second microchannels formed therein each microchannel connected to a respective source of segmenting fluid, and a transfer channel connecting the first and second microchannels;

means for sequentially applying a motive force to (i) draw a volume of the segmenting fluid into said first microchannel, (ii) stop the drawing of the segmenting fluid volume in the first microchannel, and then (iii) transport the volume of the segmenting fluid in said first microchannel away from said segmenting fluid source; and means for transferring a selected volume of fluid from said first channel through said transfer channel into said second channel.

* * * * *